(12) United States Patent
Jin et al.

(10) Patent No.: US 9,846,118 B2
(45) Date of Patent: Dec. 19, 2017

(54) PHOTOTHERMAL SPECTROSCOPY WITH HOLLOW-CORE OPTICAL FIBER

(71) Applicant: The Hong Kong Polytechnic University Shenzhen Research Institute, Shenzhen (CN)

(72) Inventors: Wei Jin, Shenzhen (CN); Yingchun Cao, Shenzhen (CN); Fan Yang, Shenzhen (CN); Hoi Lut Ho, Shenzhen (CN)

(73) Assignee: THE HONG KONG POLYTECHNIC UNIVERSITY SHENZHEN RESEARCH INSTITUTE, Shenzhen (CN)

( * ) Notice: Subject to any disclaimer, the term of this patent is extended or adjusted under 35 U.S.C. 154(b) by 0 days.

(21) Appl. No.: 15/097,732

(22) Filed: Apr. 13, 2016

(65) Prior Publication Data
US 2017/0299508 A1 Oct. 19, 2017

(51) Int. Cl.
*G01B 9/02* (2006.01)
*G01N 21/39* (2006.01)
(Continued)

(52) U.S. Cl.
CPC ............ *G01N 21/39* (2013.01); *G01J 3/45* (2013.01); *G02B 6/02328* (2013.01); *G02F 1/11* (2013.01); *G01N 2021/392* (2013.01)

(58) Field of Classification Search
CPC ............ G01N 21/39; G01N 21/3504; G01N 2021/392; G01J 3/45; G01J 3/42;
(Continued)

(56) References Cited

U.S. PATENT DOCUMENTS

| 2013/0195130 A1* | 8/2013 | Taubman | .................. H01S 5/14 |
| | | | 372/29.021 |
| 2017/0097464 A1* | 4/2017 | Challener | .......... G02B 6/02309 |

OTHER PUBLICATIONS

Kriesel et al, Hollow Core Fiber Optics for Mid-Wave and Long-Wave Infrared Spectroscopy, Apr. 2011, Paper #8018-31, SPIE Defense, Sensing, and Security in Chemical, Biological, Radiological, Nuclear, and Explosives (CBRNE) Sensing XII.*

(Continued)

*Primary Examiner* — Tarifur Chowdhury
*Assistant Examiner* — Jonathan Cook
(74) *Attorney, Agent, or Firm* — Hamre, Schumann, Mueller & Larson, P.C.

(57) ABSTRACT

The present invention provides a gas measuring method based on photothermal effect in hollow-core optical fiber comprising: filling a target gas into the core of a hollow-core optical fiber; coupling a probe light and a periodically modulated pump light into the hollow-core optical fiber; absorbing the pump light by the target gas resulting in the periodic modulation of the phase of the probe light; demodulating the phase modulation information of the probe light to obtain the concentration of the target gas, wherein the pump laser is wavelength and/or amplitude modulated. In the present invention, two lasers including a pump laser and a probe laser are used for the measurement, this approach is simple and practical. Also, the use of the hollow-core optical fiber with extremely-small core area greatly increases the optical power density, thus enhances the strength of the detected photothermal signal; this method allows ppb level gas measurement with high selectivity, and is universally suitable for the detection of gases with absorption in near-infrared.

3 Claims, 3 Drawing Sheets

(51) Int. Cl.
*G02F 1/11* (2006.01)
*G02B 6/02* (2006.01)
*G01J 3/45* (2006.01)

(58) Field of Classification Search
CPC ... G01J 3/433; G01J 2003/423; G02B 6/02328; G02F 1/11; G01B 9/02044
USPC ............................................ 356/451
See application file for complete search history.

(56) References Cited

OTHER PUBLICATIONS

Measurement of Higher Harmonics with a Lock-In Amplifier: Phase-Selective and Other Forms of Sinusoidal, Sawtooth, Square Wave, Triangular Wave, and White Noise Alternating Current Polarography, Bond et al, Analytical Chemistry, vol. 47 No. 13, Nov. 1975.*

Jin et al., "Ultra-sensitive all-fibre photothermal spectroscopy with large dynamic range," www.nature.com/naturecommunications, Received Jul. 27, 2014, Accepted Feb. 25, 2015, Published Apr. 13, 2015, DOI: 10.1038/ncomms7767, total 8 pages.

* cited by examiner

PHOTOTHERMAL SPECTROSCOPY WITH HOLLOW-CORE OPTICAL FIBER

The invention belongs to the technical field of gas measurement, in particular to a gas measuring method and system based on photothermal effect in hollow-core optical fiber.

BACKGROUND

With the development of fiber optic technologies, optical fiber gas sensors are playing an increasingly important role in environmental, safety and industrial process monitoring as well as national security applications. They have predominant features such as light weight, small size, remote detection capability, safety in hazardous environments, immunity to electromagnetic interference. Optical fiber sensor and system based on direct absorption spectrometry (DAS) is well-known and widely used in the identification of chemical species including gases. According to Beer-Lambert law, when a light with specific wavelength passes through a target gas, a portion of the light energy is absorbed by the target gas, so that the transmission light power is reduced, through which the concentration of the target gas is analyzed. The method is simple and effective, but its sensitivity is relatively low and limited by the light absorption length and a variety of noises.

Another commonly used method is tunable diode laser absorption spectrometry (TDLAS), which measures the concentration of the target gas through the change of the absorption strength when the wavelength of a tunable laser sweeps over a gas absorption line. Combined with amplitude modulation (AM) and/or wavelength modulation (WM) techniques, the method can effectively reduce the impact of noise of laser and other background noise and thus a higher sensitivity in gas measurement can be achieved. However, this method is still limited by the absorption length, a variety of methods of increasing the absorption length make the system become complex and large where high precision free-space optical components and alignments are required.

Fiber optic gas sensors with an open-path absorption cell comprising a pair of aligned miniature gradient-index (GRIN) lenses with fiber pigtails just performs a purely passive role in transferring light to and from the absorption cell but plays no part in gas sensing. Conversely, hollow-core optical fiber allows the confinement of light and gas simultaneously in its hollow-core, and this provides an excellent platform for strong light-gas interaction inside the fiber core over a long distance by which the fiber plays a more direct role in the sensing process. The fundamental mode optical field propagates in the optical fiber interacts with the gas, the absorption spectrum thereof or the attenuation of the laser power is proportional to the concentration of the gas, such that the concentration of the gas may be determined. The hollow-core optical fiber serves as an absorption cell can easily achieve a longer absorption length, thereby improving the measurement sensitivity; the optical fiber can be bent to form a fiber coil with a small diameter with negligible loss, to achieve a smaller sensor head. Thus, recently it more and more intends to use hollow-core optical fiber to measure the concentration of the gas. However, the current hollow-core optical fiber supports some high-order modes besides fundamental mode, the noise interference between the modes affects the measurement sensitivity.

Another gas measurement method based on spectral absorption is photothermal spectrometry/photoacoustic spectrometry (PTS/PAS). Distinguished from the above direct absorption measurement method, the spectrometry/photoacoustic spectrometry indirectly measures the change in temperature or in acoustic wave generated after the gas absorbs light, so as to obtain gas concentration information. Compared with the direct absorption method, a signal generated by this method is directly proportional to the amount of the absorption and is not affected by background light noise. Using high power lasers and high sensitivity acoustic or thermal detector can achieve extremely low gas concentration detection limit (ppb or even ppt). However, using this method to measure requires the use of an electrical detector, and can only achieve a single point measurement, which may not meet a variety of requirements of multi-point and remote sensing.

SUMMARY

The present invention aims at providing a gas measuring method and system based on photothermal effect in hollow-core optical fiber, which have high sensitivity and large dynamic range, to overcome the weaknesses existing in the prior art mentioned above.

To achieve the above purpose, a technical solution of the embodiment of the present invention is:

A gas measuring method based on photothermal effect in hollow-core optical fiber, comprising the following steps:

filling a target gas in the core of a hollow-core optical fiber;

coupling a probe light and a periodically modulated pump light into the hollow-core optical fiber;

absorbing the pump light by the target gas to generate a photothermal excitation effect resulting in the periodic modulation of the phase of the probe light;

demodulating the phase modulation information of the probe light to obtain the concentration of the target gas;

wherein the periodic modulation of the pump laser is a wavelength and/or amplitude modulation.

The measuring procedure of the method of the present invention uses the pump laser to excite the photothermal effect and then generates the phase modulation, the probe laser is used for phase detection. When the gas interacts with a light beam with specific wavelength, a part of the light is absorbed and the gas molecules are excited to a higher energy level and then returned to ground state through molecular collisions and other non-radiative process and generates localized heat deposition, thereby causing change of the temperature; the periodic light absorption generates periodic changes in temperature, such that the effective refractive index and length of the optical fiber of the probe light are periodically changed, and thereby periodically changing the phase of the probe light. The phase change may be demodulated by Mach-Zehnder, Fabry-Perot, Sagnac or other optical fiber interferometers, and an electrical signal proportional to the concentration of the gas is resulted, and the concentration of the target gas can be obtained.

The present invention further proposes a method for distributed detection of the concentration of a gas based on a hollow-core optical fiber, which comprises the steps of:

filling a target gas into the core of a hollow-core optical fiber;

coupling a pump light into the hollow-core optical fiber for photothermal excitation of the gas to be measured; and modulating the wavelength and/or amplitude of the pump laser periodically.

As described above, the periodically modulated pump laser periodically changes the phase of the probe light, the magnitude of the phase modulation along the length of the optical fiber reflects the concentration of the gas distributed along the length of the hollow-core optical fiber. The present invention utilizes a ϕ-OTDR technique based on the heterodyne detection to measure the magnitude of the phase modulation distributed along the length of the hollow-core optical fiber. The method combines conventional optical time domain reflectometry and coherent heterodyne detection technique to measure the magnitude of the phase modulation of the light distributed along the length of the optical fiber. The probe light is divided into two parts, one part of the probe light passes through the acousto-optic modulator by which a frequency shifted pulsed signal is generated and enters the hollow-core optical fiber. A back scattering of the pulsed probe light will be generated and combines with another part of the probe light to produce interference signal. The signal generated by a beat frequency reflects the phase changes distributed along the length of the hollow-core optical fiber, and the concentration information of the gas along the length of the hollow-core optical fiber can be obtained. The spatial resolution of the distributed measurement depends on the pulse width generated by the acousto-optic modulator, and the lower limit of the measurement of concentration depends on the phase sensitivity of the coherent detection.

The present invention also provides a gas measuring system based on photothermal effect in hollow-core optical fiber, comprising: a light source module, an optical fiber excitation detection module, a signal detection module for demodulating the interference light from the interferometer output; wherein, the light source module comprises laser drivers, a probe laser, a pump laser, a first optical isolator and a second optical isolator;

the optical fiber excitation detection module comprises a first coupler, a second coupler, a third coupler, a hollow-core optical fiber, a reference optical fiber, and an optical filter; wherein, an optical input of the first coupler is connected with the pump laser via the first optical isolator, an output of the first coupler is connected with the optical input of the third coupler via the hollow-core optical fiber;

the optical input of the second coupler is connected with the probe laser via the second optical isolator, the second coupler comprises two outputs, one output of the second coupler is connected with the input of the third coupler via the reference optical fiber, the other output of the second coupler is connected with the input of the first coupler;

the output of the third coupler is connected with the optical filter; the output of the optical filter is connected with the signal detection module.

The system of the embodiment of the present invention greatly improves the optical power density of the pump light in the measurement, such that the strength of the photothermal signal is largely enhanced; and can also reduce the influence of interference factors, and is universally suitable for the detection of gas with absorption band in the near-infrared.

DESCRIPTION OF EMBODIMENTS

To make the objectives, technical solutions, and advantages of the present invention clearer and more comprehensible, the following further describes the present invention in detail with reference to the accompanying drawings and embodiments. It should be understood that the specific embodiment described herein is merely used to explain the present invention but is not used to limit the present invention.

Figure 1:
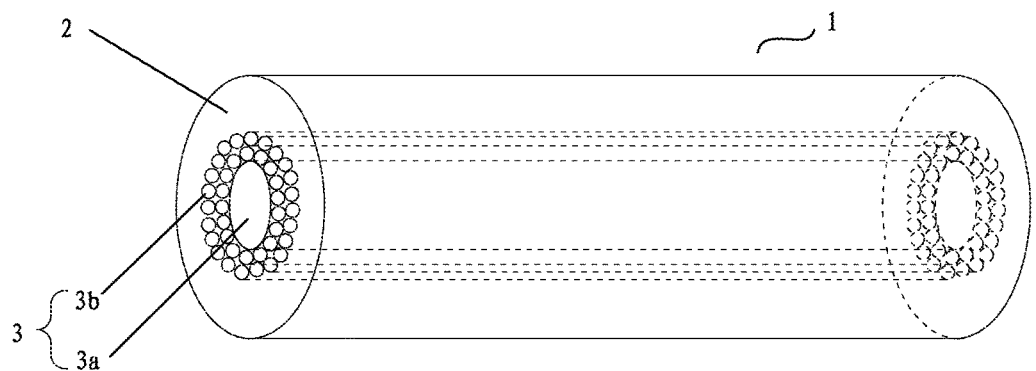
FIG. 1 is the schematic structural view of the hollow-core optical fiber of the embodiment of the present invention.
Figure 2:
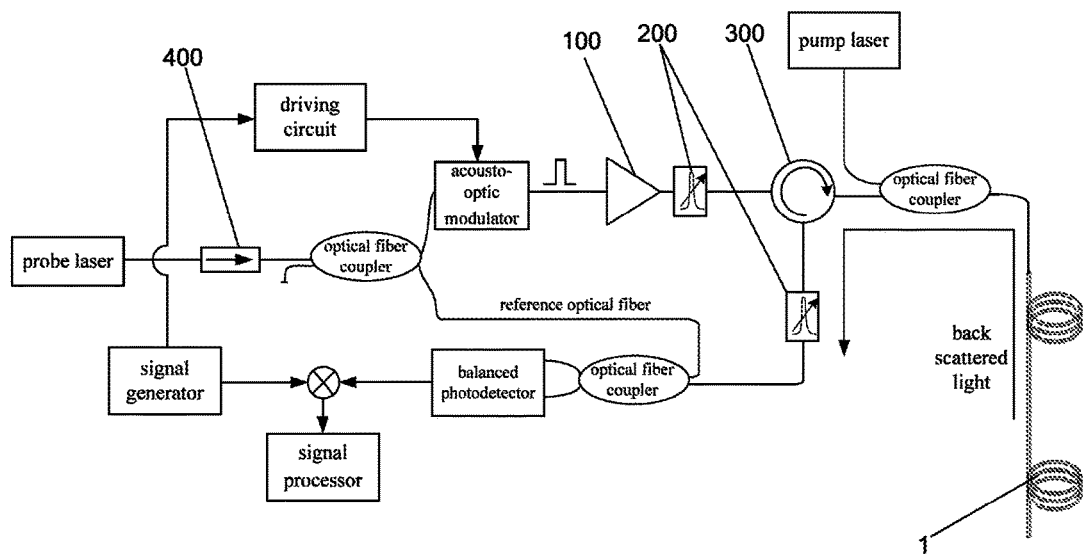
FIG. 2 is the schematic view of the distributed gas measuring based on hollow-core optical fiber of an embodiment of the present invention.
Figure 3:
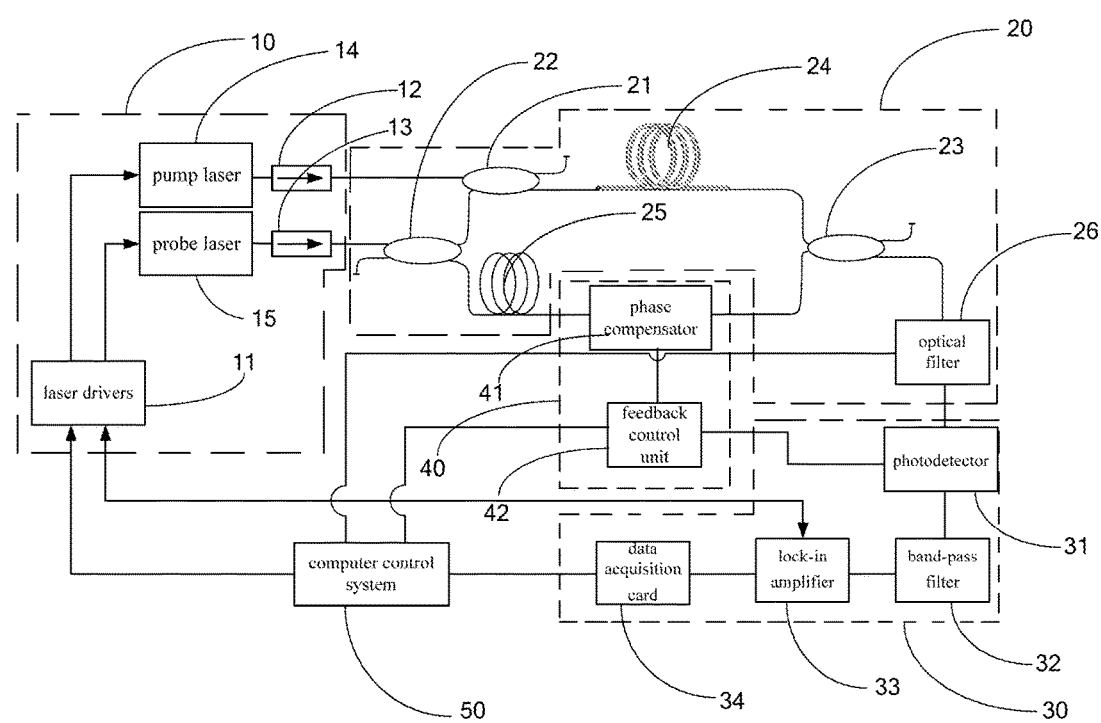
FIG. 3 shows the schematic view of the photothermal gas measuring system of an embodiment of the present invention.

An embodiment of the present invention uses a detection of phase change due to photothermal effect to replace the loss detection of conventional direct absorption to implement a gas measurement. Referring to FIGS. 1-3, the structure of the hollow-core optical fiber of the present invention is shown in FIG. 1. The hollow-core optical fiber 1 is tube shaped, and comprises an annular cladding layer 2 and a core 3 disposed in the annular cladding layer 2. The core 3 comprises a core hole portion 3a extending along the axis of the hollow-core photonic optical fiber 1, and a plurality of micro-hole portions 3b distributed around the core hole portion 3a and extending along the axis of the hollow-core optical fiber 1; the material of the annular cladding layer 2 and the micro-hole portions 3b is silica.

In the hollow-core optical fiber 1, the core hole portion 3a has a diameter of 5-20 μm, and according to the requirement of measurement, the micro-hole portions 3b may be arranged around the core hole portion 3a or arranged in an annular shape having an outer diameter of tens μm; during the measurement process, the core 3 is filled with the target gas; the annular cladding layer 2 at least ensures the strength and toughness of the whole hollow-core optical fiber 1, the hollow-core optical fiber has the diameter of about 120 μm. The structure of the hollow-core optical fiber allows coupling the light with specific wavelength into the hollow-core optical fiber 1, the light is bound by the photonic band gap effect and transmit in the core with low refractive index, therefore most of the light energy is confined in the fiber core 3. Compared with optical fiber gas sensors with evanescent field coupling, the hollow-core photonic bandgap fiber can provide extremely high light-gas interaction efficiency, thereby enhancing the gas measuring signal and the detection sensitivity.

In the gas measurement based on photothermal effect, the hollow-core optical fiber serves as a sensing medium, instead of the conventional free space gas chamber or cavity, which would have many advantages. Hollow-core photonic bandgap fiber can be coiled to small diameters (e.g., 1 cm) with minimal loss and hence can be used to develop highly compact "point" sensor. Also, the phase change of the probe light in the hollow-core optical fiber is proportional to the pump power, the length of sensing fiber, and absorption coefficient of gas molecules, and inversely proportional to the effective pump beam area. The diameter of the fundamental mode in a hollow-core photonic bandgap fiber is typically 5-10 um, more than two orders of magnitude smaller than a typical free-space beam, meaning that, for the same level of pump power, the pump intensity in a hollow-core fiber could be made significantly higher than a free-space beam. Furthermore, the fundamental mode in a hollow-core photonic bandgap fiber is well confined within the hollow core with low loss over a distance of meters to kilometers, and this can largely increase the interaction of light and gas. Hence the use of hollow-core photonic bandgap fiber would enable a relatively low power level and/or operating at a wavelength range with weaker absorption.

On account of the aforementioned advantages of the use of hollow-core optical fiber for gas concentration measurement based on photothermal effect, the present invention provides a gas measuring method using the following processes:

S10, filling a target gas into the core of a hollow-core optical fiber through free diffusion or differential pressure driven;

S20, coupling a probe light and a modulated pump light into the hollow-core optical fiber;

In this step, the pump light subjected to a periodic modulation is used for photothermal excitation, because when the gas interacts with a light beam with specific wavelength, a part of the light is absorbed and the gas molecules are excited to a higher energy level and then returned to ground state through molecular collisions and other non-radiative process and generates localized heat deposition, thereby causing the change of temperature; the periodically modulated pump light generates periodic temperature changes; when the probe light transmits through the target gas, the phase is modulated.

S30, demodulating the phase modulation information of the probe light to obtain the concentration of the target gas;

For the method of the present invention, in the step S10, the gas is filled into the core 3 of the hollow-core optical fiber 1 through free diffusion or differential pressure driven, the space in the core 3 serves as the absorption cavity for gas measurement. Furthermore, after the gas is filled into the absorption cavity in step S10, in step S20 the pump laser is coupled to the optical fibers to excite the gas.

Under the situation of fundamental mode, the intensity of the pump laser along the cross-section of the hollow-core optical fiber shows a approximate Gaussian distribution: where $P_{pump}$ is the total power of the pump laser, 2 w is the mode field diameter of the pump laser beam. Assuming that the energy is converted completely (the absorbed optical power is totally converted into heat), the heat generation rate by absorption of the light may be expressed by the following formula: $H(r,z) = A\bar{\chi}(\lambda_{pump})I(r,z)$; $\bar{\chi}(\lambda_{pump})$ is a peak normalized absorption function, A is peak absorption coefficient and equals $\alpha C$, C is relative concentration of the gas, $\alpha$ is the peak absorption coefficient when the concentration of the gas is 100%. The gas in the core of the optical fiber is heated due to heat deposition, thereby causing redistribution of the gas temperature, density and pressure, such that the effective refractive index of the fundamental mode and the length of the optical fiber are changed. Using the first-order approximation, the sum of the change rate of the effective refractive index of the fundamental mode $\eta = \Delta n_{eff}/n_{eff}$ and the change rate of the length of the optical fiber $\epsilon = \Delta l / l$ is $\eta(z)+\epsilon(z) = kA\bar{\chi}(\lambda_{pump})I_0(z)$, where k is a proportionality coefficient, after the probe light transmitted through the hollow-core optical fiber having a length of L, the phase change of the $$\Delta\varphi = \left(\frac{2\pi n_{eff}}{\lambda_{probe}} \cdot \frac{2k}{\pi w^2}\right) A\bar{\chi}(\lambda_{pump}) \cdot \int_{z=0}^{z=L} P_{pump}(z)dz = k^* A\bar{\chi}(\lambda_{pump})\bar{P}_{pump}L,$$

fundamental mode is $$I_{pump}(r) = \frac{2P_{pump}}{\pi w^2}e^{-2r^2/w^2};$$

where $\lambda_{probe}$ is the wavelength of the probe light, $n_{eff}$ is the effective refractive index of the fundamental mode in the optical fiber, $\bar{P}_{pump}$ is the average power of the pump light along the length of the optical fiber, k* is a proportionality factor. The magnitude of the phase change can be demodulated by a high sensitivity optical fiber interferometer. The concentration of the gas may be measured by detecting the phase change of the probe light. Meanwhile, as shown in FIG. 1, the probe light and pump light may transmit in the same direction or in opposite direction in the hollow-core optical fiber. The wavelengths of the pump light and probe light should be different from each other. Otherwise, when the probe light is received, it cannot be distinguished from the pump light.

In the step S30, the probe light is demodulated to obtain the phase modulation information and thus the concentration information of the target gas. In the above embodiments of the present invention, the probe light may be analyzed by Mach-Zehnder interferometer or other interferometers.

The gas detection method based on photothermal effect and hollow-core optical fiber can also be used for distributed gas measurement. In the distributed measurement, the pulsed probe light with a frequency shift is generated by an acousto-optic modulator. FIG. 2 is the schematic view of the distributed gas measuring system based on hollow-core optical fiber of an embodiment of the present invention; the part of photothermal signal excitation is similar to the foregoing description, the amplitude and/or wavelength modulated pump light is coupled into the hollow-core optical fiber through the optical fiber coupler, interacts with the target gas filled in the core to generate a photothermal phase modulation distributed along the length of the hollow-core optical fiber. The distributed measurement of the phase change in the core may be achieved by using a probe laser through φ-OTDR technology combined with heterodyne detection. Specific processes comprise: after passing through the optical isolator 400 and the optical fiber coupler, the probe light is divided into two beams, wherein the first light beam passes through the acousto-optic modulator, erbium-doped fiber amplifier 100, tunable filter 200, optical circulator 300 and an optical fiber coupler and enters the hollow-core optical fiber 1. The photothermal effect generated by gas absorption modulates the phase of the back scattered light, and then the back scattered light passes through the optical fiber coupler, optical circulator 300 and tunable filter 200 and is output in accordance with the direction of the optical path shown in FIG. 2. The second light beam passes through the reference optical fiber and is interfered with the back scattered light. The acousto-optic modulator is controlled by a signal generator and an external driving circuit which generates optical pulses with frequency shift. The erbium-doped fiber amplifier 100 is used to amplify the power of the probe light before entering the hollow-core optical fiber when the tunable filter 200 is used to reduce the ASE noise of the fiber amplifier. When the probe light transmits through the target gas, the phase of the probe light would be modulated while the backward scattered light is also subjected to the phase modulation. The probe light passing through the reference fiber is mixed with the back scattered light at the optical fiber coupler and the interference signal is then measured by a balanced detector by using the heterodyne method. The spatial resolution of the distributed detection depends on the width of optical pulses generated by the acousto-optic modulator, the distribution of the concentration of the gas along the hollow-core optical fiber can then be obtained by analyzing the heterodyne signals. As can be seen from the above steps, the distribution of the concentration of the gas along the length of the hollow-core optical fiber is obtained from the phase modulation information of the backscattered light along the length of the hollow-core optical fiber, the spatial resolution of the distributed detection depends on the width of the optical pulses generated by the acousto-optic modulator, and the measurement lower detection limit depends on the phase sensitivity of the coherent detection.

In the distributed gas measurement process, in order to allow the gas diffuse into the core at any position of the hollow-core optical fiber, micro-channels are laterally introduced on the hollow-core optical fiber. Laser beam from a femtosecond laser with optimized power reflected off a reflection mirror and passes through a focusing lens, is focused on the surface of the hollow-core optical fiber, such that silica is ablated by the laser beam from the surface to the core of the hollow-core optical fiber. Therefore, a micro-channel along the lateral of the optical fiber is formed which facilitates the target gas rapidly entering the hollow-core optical fiber. In the same way, a plurality of micro-channels can be formed along the hollow-core optical fiber. The micro-channels formed by the femtosecond laser have an average insertion loss as low as 0.03 dB per channel.

In the hollow-core optical fiber gas measuring technique of the present invention, the pump laser has narrow linewidth, the wavelength of the laser is aligned with the absorption line of the target gas, the amplitude/wavelength of the laser are modulated periodically. The probe laser is a narrow linewidth tunable laser whose output wavelength should be different from the absorption line and the wavelength of the pump laser.

To facilitate the implementation of the above detection method, the present invention provides a single-point photothermal gas measuring system, referring to FIG. 3. The system comprises: a light source module 10, an optical fiber excitation detection module 20, a signal detection module 30 for detecting the interference light at the output of the optical fiber excitation detection module 20; wherein, the light source module 10 comprises laser drivers 11, a pump laser 14, a probe laser 15, a first optical isolator 12, a second optical isolator 13; the laser drivers 11 drive the pump laser 14 and the probe laser 15;

the optical fiber excitation detection module 20 comprises a first coupler 21, a second coupler 22, a third coupler 23, a sensing optical fiber 24, a reference optical fiber 25, and an optical filter 26; wherein, the optical input of the first coupler 21 is connected with the pump laser 14 via the first optical isolator 12, an output of the first coupler 21 is connected with the optical input of the third coupler 23 via the sensing optical fiber 24;

the optical input of the second coupler 22 is connected with the output of the probe laser 15 via the second optical isolator 13, the second coupler 22 comprises two outputs, one is connected with the input of the third coupler 23 via the reference optical fiber 25, another output is connected with the input of the first coupler 21;

the output of the third coupler 23 is connected with the input of the optical filter 26; the output of the optical filter 26 is connected with the signal detection module 30.

The signal detection module 30 comprises a photodetector 31, a band-pass filter 32 for filtering out low-frequency signal, a lock-in amplifier 33 for harmonic detection, a data acquisition card 34 for acquiring the output signal from the lock-in amplifier 33; the input of the photodetector 31 is connected with the output of the optical filter 26; the input of the band-pass filter 32 is connected with the output of the photodetector 31, and the output of the band-pass filter 32 is connected with the input of the lock-in amplifier 33; the output of the lock-in amplifier 33 is connected with the data acquisition card 34.

In addition to the light source module 10, the optical fiber excitation detection module 20, and the signal detection module 30, the system further comprises a phase stabilization device 40, the phase stabilization device 40 comprises a phase compensator 41 and a feedback control unit 42 configured to give the feedback to the phase compensator 41 according to the output intensity of the optical fiber excitation detection module 20, the phase compensator 41 has a receiving terminal, and the feedback control unit 42 has a receiving and a control terminals; wherein, the receiving terminal of the phase compensator 41 is connected with the feedback control unit 42, the receiving terminal of the feedback control unit 42 is connected with the output of the photodetector 31, the control terminal of the feedback control unit 42 controls the phase compensator 41. In the present invention the phase compensator 41 may be implemented by a cylindrical piezoelectric transducer, in particular use, the reference optical fiber is wound on the cylindrical piezoelectric transducer, for adjusting and stabilizing the phase difference between the sensing optical fiber and the reference optical fiber.

Figure 4:
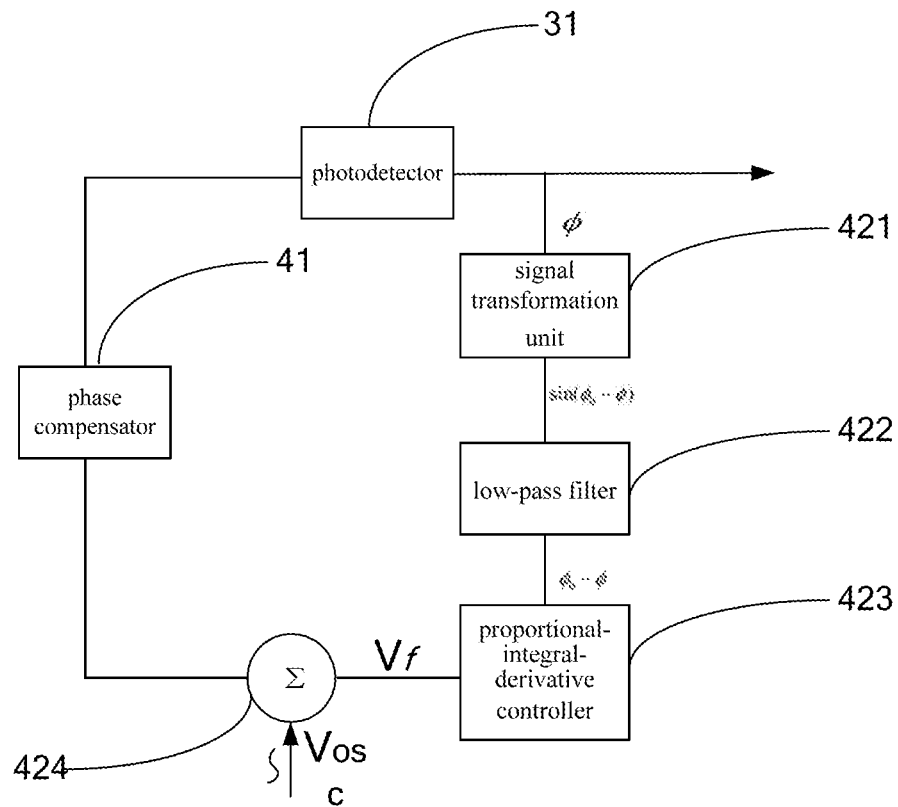
FIG. 4 is a schematic structural view of the feedback control unit in FIG. 3.

Furthermore, in order to ensure accurate phase compensation, the feedback control unit 42 comprises an signal transformation unit 421 configured to calculate the required phase compensation according to the output intensity of the optical fiber excitation detection module 20, a low-pass filter 422 is used to convert a phase compensation information calculated by the signal transformation unit 421 into a phase error signal, a proportional-integral-derivative controller 423 configured to send a feedback voltage signal to the phase compensator 41 according to the phase error signal, and a signal superposition device 424 configured to superpose the feedback voltage signal with a preset AC signal. FIG. 4 is a schematic structural view of the feedback control unit 42. The input of the signal transformation unit 421 is connected with the output of the photodetector 31 and the output of the signal transformation unit 421 is connected with the input of the low-pass filter 422; the output of the low-pass filter 422 is connected with the input of the proportional-integral-derivative controller 423; the output of the proportional-integral-derivative controller 423 is connected with the input of the signal superposition device 424; the output of the signal superposition device 424 is connected with the receiving terminal of the phase compensator 41.

In order to prevent the light back to the pump laser 14 and probe laser 15 in the light source module 10, a first optical isolator 12 and a second optical isolator 13 are used, respectively. A distributed feedback laser (DFB) may be used as the pump laser 14 in the light source module 10. Take the acetylene gas for example, the wavelength of the pump laser 14 may be 1.53 μm, corresponding to the absorption line of v1+v3 overtone absorption band of the acetylene gas, while a laser current is modulated periodically. After passing through the first optical isolator 12, the periodically modulated light from the pump laser 14 is coupled into the sensing optical fiber 24 via the first optical isolator 12 and the first optical fiber coupler 21, and interacts with the target gas filled in the sensing optical fiber 24. The probe laser 15 may be a tunable external cavity diode laser, and the light from the laser passes through the second optical isolator 13, a second optical fiber coupler 22 and the first optical fiber coupler 21 and enters the sensing optical fiber 24, to detect the phase changes inside the hollow-core photonic band gap fiber. The amplitude/wavelength of the pump laser 14 is periodically modulated by a built-in signal generator of lock-in amplifier 33, while the wavelength of the probe laser 15 is fixed at 1.55 μm. Furthermore, the reference optical fiber 25 and the sensing optical fiber 24 are used to form a Mach-Zehnder interferometer to measure the phase changes of the probe light in the sensing optical fiber 24. Specifically, a hollow-core optical fiber served as the sensing optical fiber 24 is combined with a conventional single-mode optical fiber that is the reference optical fiber 25 to form the Mach-Zehnder interferometer, and then the probe light is respectively coupled into the sensing optical fiber 24 and the reference optical fiber 25 via the second coupler 22. Then the probe light output by the sensing optical fiber 24 whose phase is changed and the probe light output by the reference optical fiber without phase change are coupled into the third coupler 23 to form the interference light. The phase modulation information of the interference light may be converted to amplitude change, the amplitude change can then be detected by the photodetector 31.

Meanwhile, in the above-mentioned Mach-Zehnder interferometer, in order to maximize the conversion from the phase modulation signal generated by the photothermal effect to the amplitude modulation signal, the differential phase DC component between the sensing and reference beams needs to be stabilized at the quadrature point of ±90°. Therefore, in order to ensure the phase stability, the phase stabilization device 40 is used in the present invention to stably control the phase. Specifically, $\cos(\phi-\phi_0)$ can be derived from the output intensity of the interferometer where $\phi$ contains the photothermal signal and $\phi_0$ (herein set to 90°) is the target phase difference. Then, $\sin(\phi-\phi_0)$ can be calculated by the signal transformation unit 421:

$$\sin(\phi_0-\phi)=\sin(\phi_0)\cos(\phi)-\cos(\phi_0)\sin(\phi)$$

When the actual phase is close to the target phase, it can be considered that $\sin(\phi_0-\phi)\approx\phi_0-\phi$. Such operation is used to represent the information of the values for phase compensation, and is filtered by the low-pass filter 422 to obtain phase error signal. Then a feedback voltage signal is generated by the proportional-integral-derivative controller 423 according to the phase error value to control the phase compensator 41 to compensate the phase. However, when the feedback voltage signal is sent to the phase compensator, the signal superposition device 424 is needed to superpose the feedback voltage signal and a preset small AC signal and send the superposed signal to the phase compensator 41. In the embodiment, the phase compensator 41 is implemented by a cylindrical piezoelectric transducer (PZT). When a voltage signal is applied to the electrode of the PZT, the PZT deforms, thereby changing the length of the optical fiber wound on the PZT, thereon, further changing the phase along the optical fiber. Other phase stabilization or demodulation methods may also be used to obtain the photothermal effect induced phase change.

However, the light from the sensing optical fiber 24 also comprises pump light which may be filtered out by the optical filter 26. Then, photodetector 31 converts the interference light with phase signal to a voltage signal. The voltage signal passes through the band pass filter 32 to filter out the noise with other frequencies, the lock-in amplifier 33 for harmonic detection, and the data acquisition card 34 for acquiring data from the lock-in amplifier 33. In addition, a computer control system 50 is used to control the light source module 10, the optical fiber excitation and detection module 20, the signal detection module 30 and to process the data acquired from the data acquisition card 34.

Figure 5:
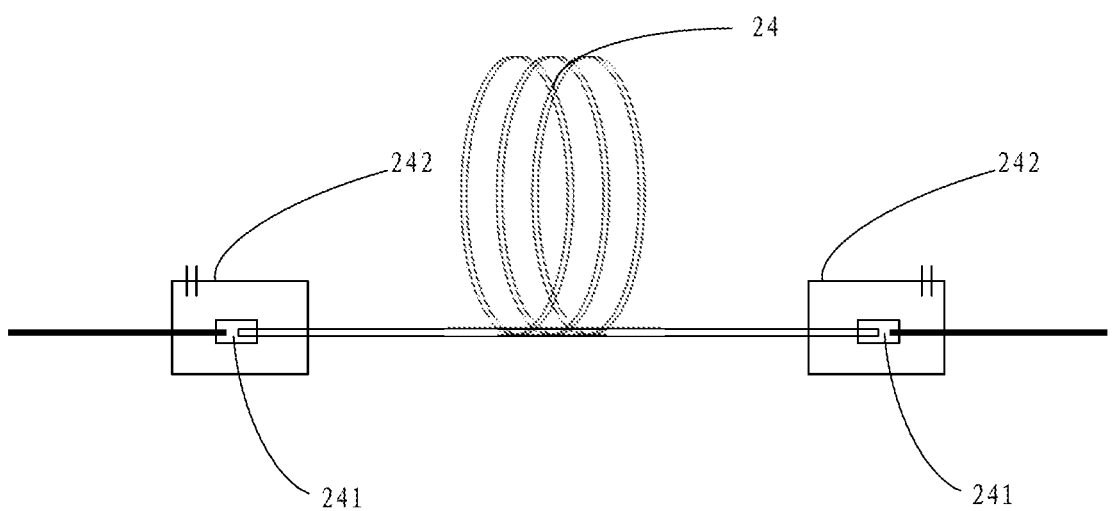
FIG. 5 is a schematic structural view of the connection of the sensing optical fiber and the optical path in FIG. 3.

In the above system, all optical components and devices are connected by using conventional single-mode optical fiber except the sensing optical fiber 24 which acts as absorption cell for gas-light interaction at the present invention. Two ends of the sensing optical fiber 24 may be connected to the single-mode optical fiber through mechanical connection or fusion splicing, etc., FIG. 5 is a schematic structural view of the connection between the sensing optical fiber 24 and the conventional single-mode fiber in the optical path as shown in FIG. 3. The connection may be implemented in two ways, one is that small gaps 241 are left at the connection between the sensing optical fiber 24 and the single-mode optical fiber in the optical path, the gap 241 is controlled to have a width of about 20 μm, and the connections are respectively enclosed in two micro air chambers 242, and each of the air chambers 242 has a gas inlet/outlet connecting with the outside environment, the target gas enters the sensing optical fiber 24 through the inlet of the air chamber 242. In addition to the above described method, the connect of the sensing optical fiber 24 and the single-mode optical fiber in the optical path may be fusion spliced, and then the sensing optical fiber 24, is drilled laterally by using the femtosecond laser to allow the target gas getting into the hollow core of the sensing optical fiber 24.

To understand the above described apparatus, the present invention herein takes the acetylene gas as an example. For the concentration measurement of acetylene gas, a standard gas with a volume concentration of 10 ppm (ppm=parts per million) is filled into the sensing optical fiber 24 through differential pressure; the P(9) absorption line of acetylene gas having the wavelength of 1,530.37 nm is selected as the wavelength of the pump laser 14, the spectral line intensity of acetylene molecules at this wavelength is $1.211\times10^{-20}$ $cm^{-1}$/(molecule $cm^{-2}$), which corresponds to the spectral line intensity of 0.3 $cm^{-2}$/atm of the gas at room temperature; the pump laser is subjected to wavelength/amplitude modulation, the modulation frequency is 50 kHz, the lock-in amplifier detects a second harmonic signal generated by the wavelength/amplitude modulation. By scanning the wavelength of the pump light, the second-harmonic photothermal signal spectrum changing with wavelength can then be measured. Time constant and the slope of the filter of the lock-in amplifier are set to 0.1 s and 18 dB/Oct, respectively. For measuring the value of the noise, the wavelength of pump laser is adjusted to stay away from the gas absorption peak, the time constant of the lock-in amplifier is set to 1 s, the slope of the filter is maintained at 18 dB/Oct, the value of the noise may be obtained by measuring the second harmonic signal with over time. A background signal (base signal) away from the absorption line is caused by residual pump amplitude modulation. When the power of pump light entering the 10-m-long hollow-core optical fiber is 15.3 mW, the signal to noise ratio is calculated to be 5270 by calculating the peak-to-peak value of the second harmonic signal and the signal noise away from the absorption peak, the corresponding minimum detectable concentration of acetylene is 2 ppb (ppb=part per billion). With 10-m-long sensing fiber, the acetylene gas with ppb level sensitivity has been achieved.

The foregoing descriptions are merely exemplary embodiment of the present invention, but are not intended to limit the present invention to it. Any modification, equivalent replacement, or improvement made without departing from the spirit and principle of the present invention shall fall within the protection scope of the present invention.

What is claimed is:

1. A gas measuring method based on photothermal effect in hollow-core optical fiber, comprising the following steps:
    filling a target gas into the core of a hollow-core optical fiber;
    coupling a probe light and a periodically modulated pump light into the hollow-core optical fiber;
    absorbing the modulated pump light by the target gas to generate a photothermal excitation effect resulting in the periodic modulation of the phase of the probe light;
    demodulating the phase modulation information of the probe light to obtain the concentration of the target gas;
    wherein the periodic modulation of the pump laser is wavelength and/or amplitude modulation,
    wherein the probe light is a pulsed light,
    wherein the obtained concentration of the target gas is a distributed gas concentration along the length of the hollow-core optical fiber, and
    wherein demodulating the phase modulation information of the probe light comprises demodulating the phase modulation information of the back scattered pulsed probe light in the hollow-core optical fiber.

2. The gas measuring method based on photothermal effect in hollow-core optical fiber of claim 1, wherein demodulating the phase modulation information of a back scattered pulsed probe light in the hollow-core optical fiber comprises the steps of:
    combining the phase-modulated back scattered probe light with the unmodulated probe light to obtain an interference light, and
    obtaining phase changes of the back scattered light distributed along the length of the hollow-core optical fiber by demodulating the signal generated by a beat frequency of the interference light, to obtain the distributed concentration information of the target gas along the length of the optical fiber.

3. The gas measuring method based on photothermal effect in hollow-core optical fiber of claim 2, wherein the probe light comprises a first part and a second part;
    wherein the first part is a frequency-shifted pulsed light generated by an acousto-optic modulator, and
    wherein the second part serves as an unmodulated probe light which interferes with the phase-modulated back scattered probe light.

* * * * *